United States Patent
Smith et al.

(10) Patent No.: US 9,744,014 B2
(45) Date of Patent: Aug. 29, 2017

(54) ORAL ENGAGEMENT ASSEMBLIES

(75) Inventors: Rebecca Smith, Glen Ellyn, IL (US); Thomas J. Blair, Chesterfield, MO (US); J. William Nottingham, Westlake, OH (US)

(73) Assignee: Nestec S.A., Vevey (CH)

( * ) Notice: Subject to any disclaimer, the term of this patent is extended or adjusted under 35 U.S.C. 154(b) by 263 days.

(21) Appl. No.: 13/879,303

(22) PCT Filed: Oct. 6, 2011

(86) PCT No.: PCT/US2011/001727
§ 371 (c)(1),
(2), (4) Date: Jun. 13, 2013

(87) PCT Pub. No.: WO2012/050602
PCT Pub. Date: Apr. 19, 2012

(65) Prior Publication Data
US 2013/0266905 A1  Oct. 10, 2013

Related U.S. Application Data

(60) Provisional application No. 61/455,152, filed on Oct. 15, 2010.

(51) Int. Cl.
*A61D 5/00* (2006.01)
*A61C 19/04* (2006.01)
(Continued)

(52) U.S. Cl.
CPC .............. *A61D 5/00* (2013.01); *A01K 15/026* (2013.01); *A61B 10/0051* (2013.01);
(Continued)

(58) Field of Classification Search
CPC ...... A61D 5/00; A61B 5/682; A61B 10/0051; A61C 17/0211; A61C 19/04; A01K 15/026
(Continued)

(56) References Cited

U.S. PATENT DOCUMENTS 3,916,877 A * 11/1975 Beckman ...................... 600/483
3,935,744 A * 2/1976 Beckman ...................... 600/549
(Continued)

FOREIGN PATENT DOCUMENTS

WO       WO 97/20502     *  6/1997    ......... A61B 10/0051

OTHER PUBLICATIONS

International Search Report for International Application No. PCT/US2011/001727 dated Jan. 30, 2012.
(Continued)

*Primary Examiner* — Cris L Rodriguez
*Assistant Examiner* — Hao D Mai
(74) *Attorney, Agent, or Firm* — Julie M. Lappin; Aaron J. Morrow

(57) ABSTRACT

Oral engagement assemblies and methods of using the oral engagement assemblies are provided. In a general aspect, the oral engagement assembly includes a mouthpiece having a handle and a support attached to the handle. A diagnostic receptacle is insertable into the mouth-piece to form the oral engagement assembly. One or more diagnostic sensors can be fixedly or releasably inserted into the diagnostic receptacle. Kits useful for making the oral engagement assemblies and using such oral engagement assemblies for diagnosing a condition or disease in the animal are also provided.

23 Claims, 4 Drawing Sheets

(51) Int. Cl.
*A01K 15/02* (2006.01)
*A61B 10/00* (2006.01)

(52) U.S. Cl.
CPC ...... *A61C 19/04* (2013.01); *A46B 2200/1086* (2013.01); *A61B 2010/0003* (2013.01); *A61B 2010/0006* (2013.01); *A61B 2010/0087* (2013.01)

(58) Field of Classification Search
USPC ................ 433/1, 229; 15/22.1, 167.1–167.2; 600/582
See application file for complete search history.

(56) References Cited

U.S. PATENT DOCUMENTS

| | | | | |
|---|---|---|---|---|
| 3,968,690 | A * | 7/1976 | Blouin | G01K 5/22 374/151 |
| 4,202,353 | A * | 5/1980 | Hirsch et al. | 600/537 |
| 5,711,759 | A * | 1/1998 | Smith | A61J 17/00 601/139 |
| 5,922,614 | A * | 7/1999 | Cesarczyk | G01N 1/02 422/411 |
| 6,372,516 | B1 * | 4/2002 | Sun | 436/518 |
| 6,582,224 | B1 * | 6/2003 | Lilien et al. | 433/1 |
| 6,679,257 | B1 * | 1/2004 | Robertson et al. | 128/204.18 |
| 6,839,636 | B1 * | 1/2005 | Sunshine et al. | 702/22 |
| 6,840,911 | B2 * | 1/2005 | Sangha | 600/582 |
| 6,875,185 | B2 * | 4/2005 | Wong et al. | 600/584 |
| 7,333,020 | B2 * | 2/2008 | Cohen et al. | 340/573.1 |
| 7,459,125 | B1 * | 12/2008 | Stankov et al. | 422/412 |
| 7,695,953 | B2 * | 4/2010 | Gould et al. | 435/287.2 |
| 2004/0082878 | A1 * | 4/2004 | Baldwin et al. | 600/573 |
| 2004/0184954 | A1 * | 9/2004 | Guo et al. | 422/56 |
| 2006/0013738 | A1 * | 1/2006 | Ramsey | 422/99 |
| 2006/0141421 | A1 * | 6/2006 | Braunecker et al. | 433/215 |
| 2007/0106172 | A1 * | 5/2007 | Abreu | 600/549 |
| 2009/0024058 | A1 | 1/2009 | Blowick | |
| 2009/0208898 | A1 * | 8/2009 | Kaplan | 433/80 |
| 2009/0221884 | A1 * | 9/2009 | Ryan | 600/301 |
| 2012/0021375 | A1 * | 1/2012 | Binner et al. | 433/89 |

OTHER PUBLICATIONS

International Written Opinion for International Application No. PCT/US2011/001727 dated Jan. 30, 2012.

* cited by examiner

ORAL ENGAGEMENT ASSEMBLIES

CROSS REFERENCE TO RELATED APPLICATIONS

This application is a national stage application under 35 USC §371 of PCT/US2011/001727 filed on 6 Oct. 2011 and claims priority to U.S. Provisional Application. No. 61/455,152 filed 15 Oct. 2010, the disclosures of which are incorporated herein by this reference.

BACKGROUND OF THE INVENTION

Field of the Invention

The invention relates generally to oral engagement assemblies and particularly to oral engagement assemblies having mechanisms for cleaning teeth and for screening and diagnosing animal health.

Description of Related Art

Animal caregivers are looking for convenient, easy, and quick ways to proactively manage the oral and general health of animals, particularly pets. Dental health is a major issue and concern of animal caregivers. Typical products for improving pet dental health include hard or crunchy pet treats (e.g., biscuits) or pet products made from a chewable material (e.g., rawhide). Similarly, various pet foods can be used to improve dental health, e.g., U.S. Pat. No. 7,592,031, U.S. Pat. No. 7,125,574, U.S. Pat. No. 6,904,870, and U.S. Pat. No. 6,841,178.

Caregivers also want to easily screen for the early stages of common health issues associated with dental health and with various diseases and conditions such as digestive system and diabetes. However, current diagnostic tools can be costly and complicated. Similarly, while there are many products that help to clean a pet's teeth with mechanical action, no single product exists today that combines this action with the ability to use the pet's saliva to screen for common health issues like dental hygiene, digestive problems, or diabetes. There is, therefore, a need for novel oral engagement assemblies having mechanisms for cleaning teeth and screening and diagnosing animal health.

SUMMARY OF THE INVENTION

It is, therefore, an object of the invention to provide oral engagement assemblies useful for diagnosing a condition or disease in an animal of an animal.

It is another object of the invention to provide oral engagement assemblies useful for strengthening the teeth.

It is a further object of the invention to provide oral engagement assemblies that have insertable diagnostic sensors suitable for diagnosing a condition or disease in an animal.

It is yet another object of the invention to provide methods of collecting oral fluid of an animal using an oral engagement assembly.

It is still another object of the invention to provide methods of strengthening the teeth of an animal using an oral engagement assembly.

It is another object of the invention to provide methods of diagnosing a condition or disease in an animal using an oral engagement assembly.

These and other objects are achieved using an oral engagement assembly including a mouth-piece and a diagnostic receptacle. In preferred embodiments, the oral engagement assembly includes a mouth-piece comprising a handle defining an opening and a support attached to the handle. A diagnostic receptacle is insertable into the opening of the handle and the support. One or more diagnostic sensors can be fixedly or releasably inserted into the diagnostic receptacle. The oral engagement assemblies can be used to improve the oral hygiene and screen for and diagnose animal health.

Additional and further objects, features, and advantages of the invention will be readily apparent to those skilled in the art.

DETAILED DESCRIPTION OF THE INVENTION

Definitions

The term "single package" means that the components of a kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof. A single package may contain a mouth-piece, a diagnostic receptacle, a diagnostic chart, a diagnostic tool for oral fluid, and the like as described herein that can be physically associated such that they are considered a unit for manufacture, distribution, sale, or use.

The term "virtual package" means that the components of a kit are associated by directions on one or more physical or virtual kit components instructing the user how to obtain the other components, e.g., a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The term "diagnostic sensor" means any device, compound or material that can be used to indicate the health or condition of an animal upon being exposed to a bodily component of an animal. For example, the bodily component can be oral fluid or the breath of the animal. The indication can be a change in color, pattern, shape, etc., or any other suitable change that corresponds with a particular condition or change in condition of the animal.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "an oral assembly" or "a method" includes a plurality of such "oral assemblies" or "methods". Similarly, the words "comprise", "comprises", and "comprising" are to be interpreted inclusively rather than exclusively. Likewise, the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The devices, assemblies, kits, methods, compositions and other advances disclosed here are not limited to particular methodology, protocols and reagents described herein because, as the skilled artisan will appreciate, they may vary. Further, the terminology used herein is for the purpose of describing particular embodiments only, and is not intended to, and does not, limit the scope of that which is disclosed or claimed.

The Invention

Figure 1:
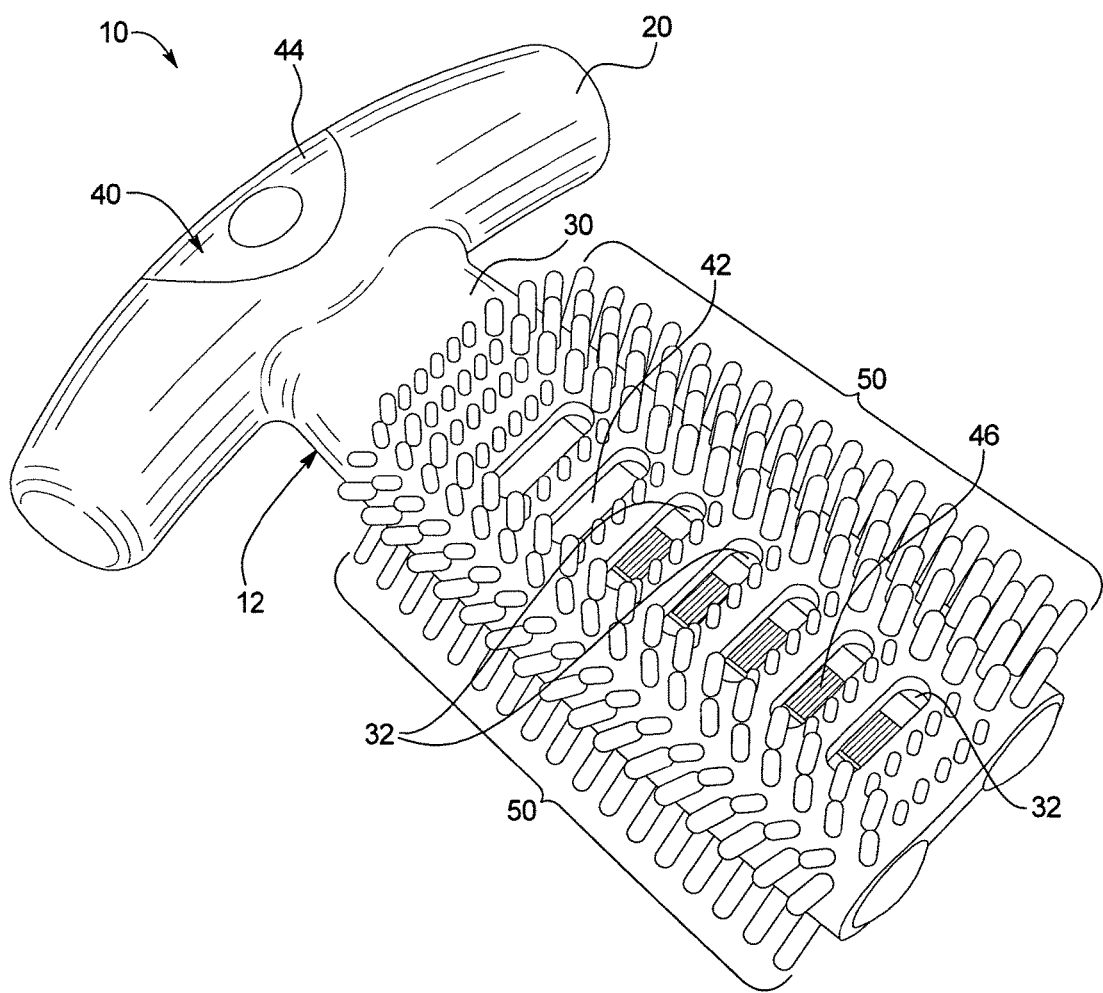
FIG. 1 shows a perspective view of an oral engagement assembly in an embodiment of the invention.
Figure 2:
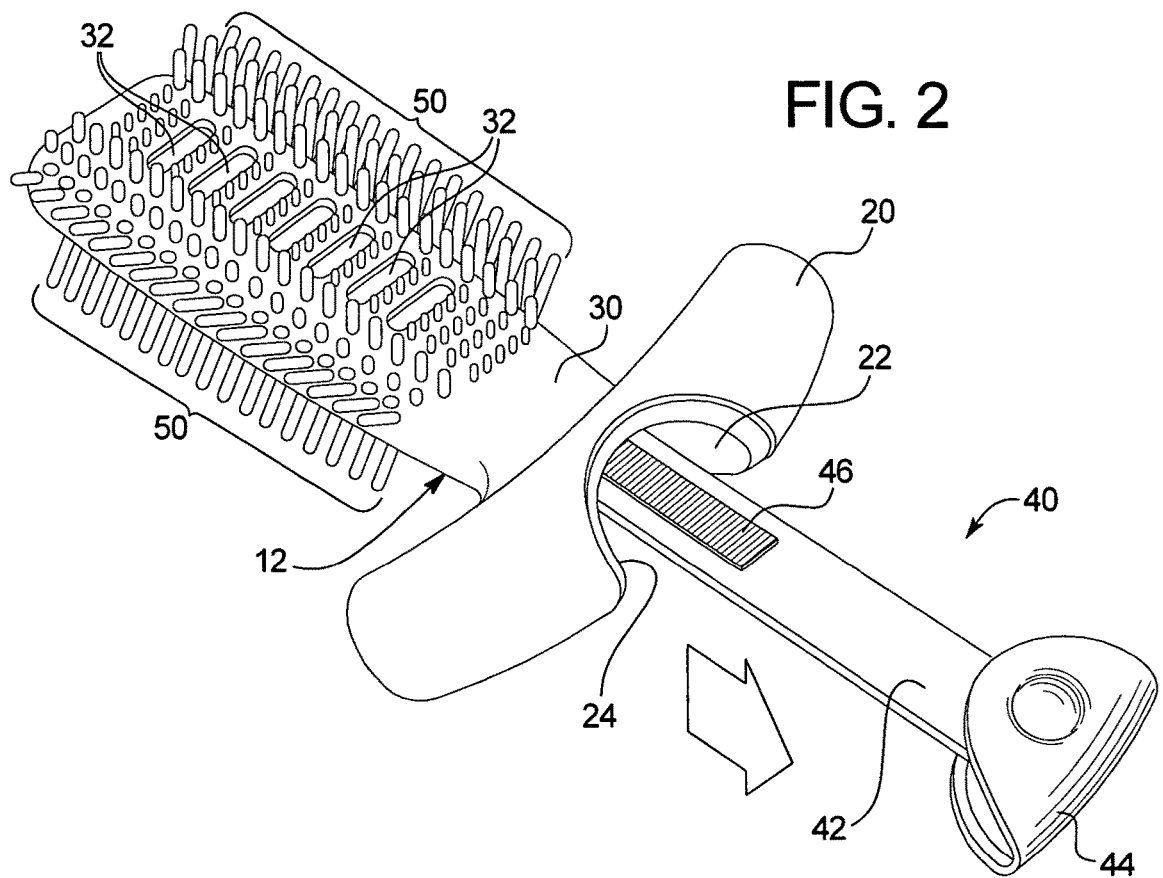
FIG. 2 shows a perspective view of the diagnostic receptacle and diagnostic sensor separated from the mouth-piece of the oral engagement assembly.

In one aspect, as illustrated in FIGS. 1-2, the invention provides an oral engagement assembly 10 including a mouth-piece 12 having a handle 20 defining an opening 22 and a support 30 attached to handle 20. Support 30 defines a passageway and includes one or more apertures 32. Oral engagement assembly 10 further includes a diagnostic receptacle 40 insertable into opening 22 of handle 20 and the passageway of support 30. Handle 20 can be any suitable configuration and include any suitable textured grip allowing it to be easily grasped by a user.

As further shown in FIGS. 1-2, support 30 may include a plurality of bristles 50. Bristles 50 are constructed and arranged for brushing along the teeth of the animal when the support is in the animal's mouth. Bristles 50 can be any suitable size, shape or amount for optimizing the mechanical dental cleaning of the animal's teeth and/or massaging the gums of the animal. In addition, bristles 50 can be made of any suitable material such as rubber, plastic, etc., to provide sufficient strength, flexibility and durability to be chewed on by the animal. In an embodiment, support 30 and/or bristles 50 can be coated with a deodorant, teeth cleaning product, or oral antiseptic.

Figure 3:
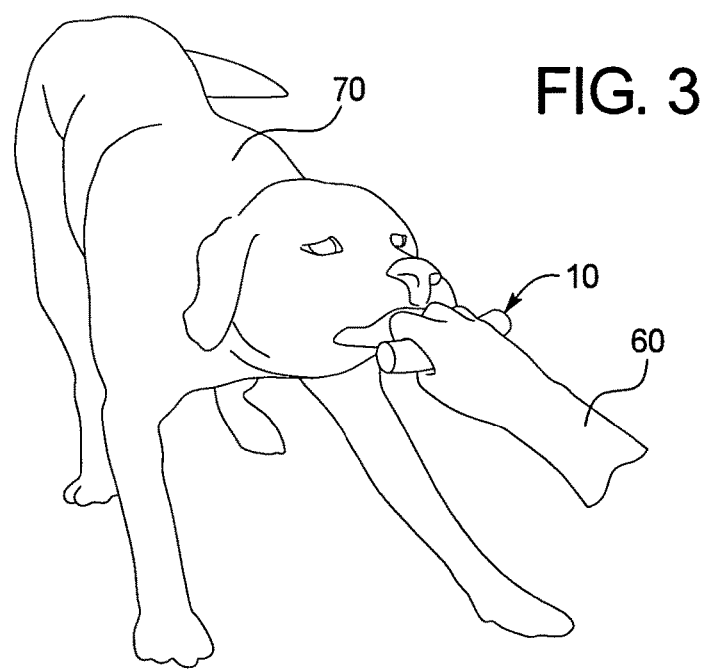
FIG. 3 shows a user and an animal utilizing the oral engagement assembly.

During use as shown in FIG. 3, a user 60 inserts oral engagement assembly 10 into the mouth of a pet animal such as a dog 70, typically by engaging in playful activity with the animal wherein the animal bits the assembly and tugs on the assembly while the user holds the handle. Dog 70 can firmly bite down on oral engagement assembly 10 while user 60 moves oral engagement assembly 10 back and forth, side to side, or up and down so as to rub against the teeth of dog 70. Moreover, during this action, oral fluid from dog 70 can conveniently pass through apertures 32 on support 30 of oral engagement assembly 10 to be collected within oral engagement assembly 10 and be used for diagnostic purposes in assessing the animal's heath, e.g., the oral fluid contacts a sensor in the assembly or is collected for removal from the assembly and then tested.

In an embodiment, diagnostic receptacle 40 includes a gripping portion 44 attached to an elongated stick 42 including one or more diagnostic sensors 46. In an embodiment shown in FIG. 2, handle 20 includes a receiving groove 24 engaging gripping portion 44 of diagnostic receptacle 40, which can be shaped to fit within receiving groove 24. Gripping portion 44 can be attached to receiving groove 24 using any suitable mechanisms such as, for example, a snap-fit so as to not easily detach when oral engagement assembly 10 is being used.

Figure 4:
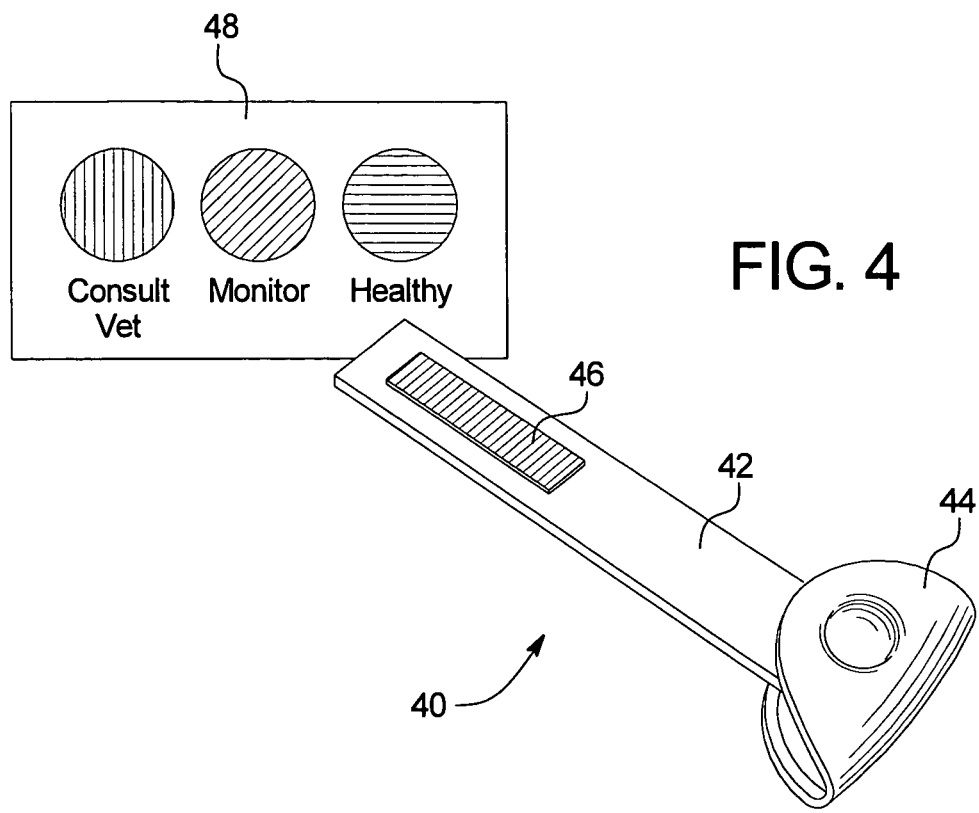
FIG. 4 shows a perspective view of the diagnostic receptacle and the diagnostic sensor in an embodiment of the invention.

As shown in FIG. 4, diagnostic receptacle 40 can include one or more diagnostic sensors 46. Diagnostic sensor 46 can be any suitable sensor that reacts with the animal's saliva or breath and is able to indicate the animal's health condition or an animal disease. Diagnostic sensor 46 can be releasably inserted in or attached to diagnostic receptacle 40 in any suitable manner. In this configuration, diagnostic sensor 46 can be easily removed from diagnostic receptacle 40 and replaced without breaking diagnostic receptacle 40. Thus, diagnostic receptacle 40 can be reused multiple times with replicable sensors.

Alternatively, diagnostic receptacle 40 can comprise at least one diagnostic sensor 46 fixedly attached to diagnostic receptacle 40 to form an integrated diagnostic device. In this configuration, for example, diagnostic sensor 46 is not able to be removed from diagnostic receptacle 40 without breaking diagnostic receptacle 40.

In an embodiment, diagnostic sensor 46 can be in the form of a test strip (e.g., visual test strips, saliva activated test strips, or glucose test strips) to indicate a health condition or disease of the animal. For example, as shown in FIG. 4, the pattern of diagnostic sensor 46 can change when contacted with the animal's saliva or breath to indicate the health condition of the animal. The pattern (or color) of diagnostic sensor 46 after exposure to the oral fluid or breath of the animal can be compared to a diagnostic chart 48 that indicates what type of heath an animal might have based on the pattern (or color) of diagnostic sensor 46. Diagnostic chart 48 can be separate from diagnostic receptacle 40 or it can be incorporated as part of diagnostic receptacle 40 (e.g., attached to a portion of elongated stick 42).

Diagnostic sensor 46 can be made to measure or diagnose any desired health condition or change in health of the animal and any animal disease. Such health conditions or diseases can be dental, digestion, diabetes, halitosis, or combinations thereof or any other health conditions associated with animals for which a sensor is available. Non-limiting examples of diagnostic tests that can be performed include plaque and tartar build-up, microflora load, nutrient absorption, and glucose levels. In an embodiment, diagnostic receptacle 40 includes a breath tester.

An animal owner or caregiver can use oral engagement assembly 10 with diagnostic receptacle 40 one or more times (e.g., daily) by inserting diagnostic sensor 46 into diagnostic receptacle 40, engaging the animal, collecting the fluid (saliva), and testing the fluid for whatever (e.g., glucose). More specifically, the animal caregiver takes oral engagement assembly 10, removes diagnostic receptacle 40 from oral engagement assembly 10, inserts diagnostic sensor 46 into diagnostic receptacle 40, engages the animal with oral engagement assembly 10, allows oral fluid from the animal to contact diagnostic sensor 46 in diagnostic receptacle 40, observes diagnostic sensor 46 (e.g., for a color change), and makes a diagnosis based on the status of diagnostic sensor 46 (e.g., the color change or lack thereof indicates a disease or condition).

The animal caregiver can remove diagnostic sensor 46 from diagnostic receptacle 40, wash diagnostic receptacle 40, save diagnostic receptacle 40, and use diagnostic receptacle 40 again the next day or at another suitable time by inserting a new diagnostic sensor 46 into diagnostic receptacle 40 and engaging the animal as previously described. In this regard, the reusable oral engagement assembly 10 can be sold or given away separately from the sale of diagnostic sensor 46 (e.g., test strips) that are used in conjunction with oral engagement assembly 10.

Alternatively, oral engagement assembly 10 can be sold in conjunction with the previously described integrated diagnostic device already having the diagnostic sensor fixedly attached to the diagnostic receptacle. The integrated diagnostic device can be convenient for the animal caregiver because the caregiver can insert such integrated diagnostic device into the oral engagement assembly instead of the diagnostic receptacle and the separate diagnostic sensor. In this situation, the caregiver would remove the diagnostic receptacle and replace it with the integrated diagnostic device, use the integrated diagnostic device, and toss it (or send it to a laboratory or hospital for testing).

Figure 5:
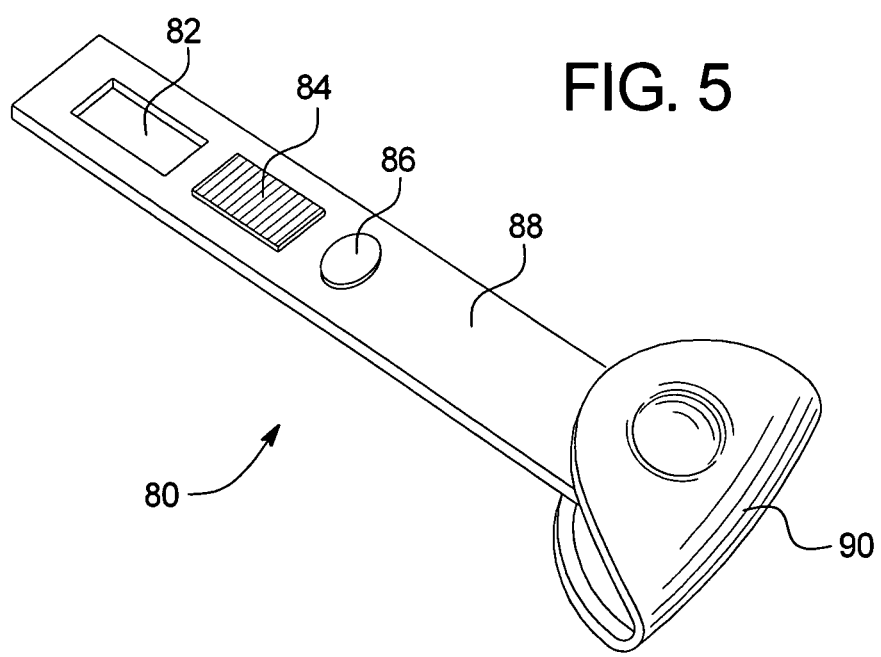
FIG. 5 shows a perspective view of the diagnostic receptacle having a fluid capturing mechanism in an embodiment of the invention.

In another aspect, as illustrated in FIG. 5, a diagnostic receptacle 80 for the oral engagement assembly can include one or more fluid capturing mechanisms such as a tray 82 and/or a sponge 84 in addition to or in place of a diagnostic sensor 84. In this embodiment, diagnostic receptacle 80 is configured as an "oral sample collector." Diagnostic receptacle 80 can include a suitable gripping portion 90 attached to an elongated stick 88 on which fluid tray 82, sponge 86 and/or diagnostic sensor 84 reside.

The fluid capturing mechanism can be also be any suitable mechanism for capturing and collecting oral fluid when the oral engagement assembly is placed inside the mouth of the animal. Oral fluid can then be taken from the oral sample collector (e.g., fluid capturing mechanisms) and subsequently tested using any suitable diagnostic tool. For example, during use, an animal caregiver can either: (1) take the oral sample collector with the fluid to a location where the fluid can be (a) tested in the oral sample collector or (b) removed from the oral sample collector and tested, or (2) seal the oral sample collector and send it to a remote location (e.g., mail it to a laboratory or hospital) where the oral fluid can be tested as in (a) or (b).

Figure 6:
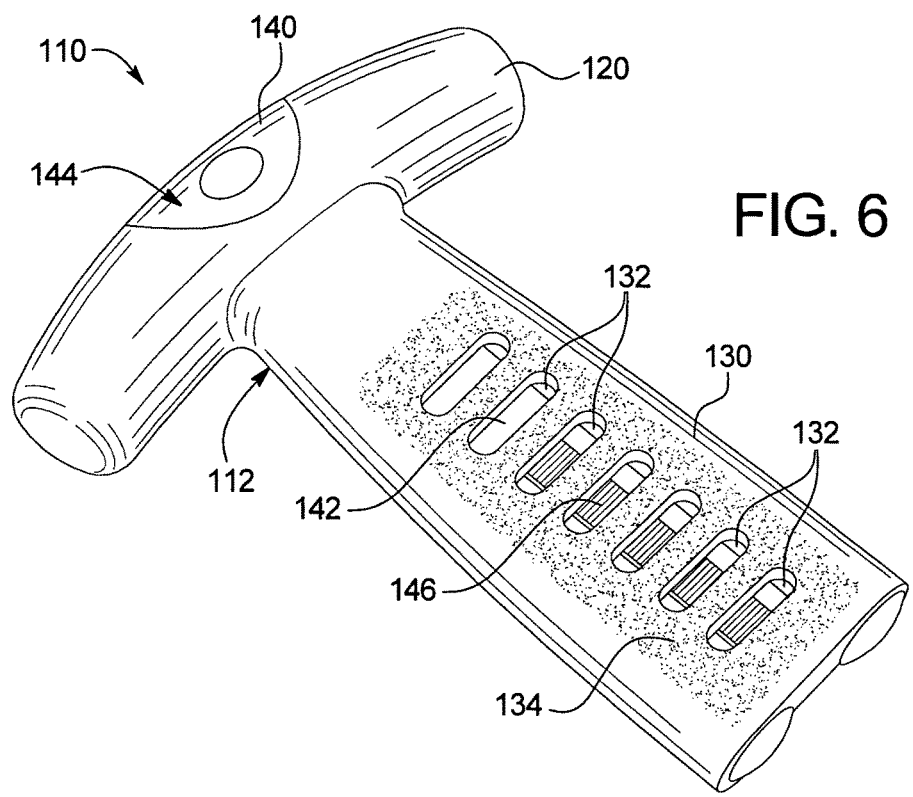
FIG. 6 shows a perspective view of an oral engagement assembly in a second embodiment of the invention.

In another aspect, as illustrated in FIG. 6, the invention provides an oral engagement assembly 110 including a mouth-piece 112 having a handle 120 defining an opening and a support 130 attached to handle 120. Support 130 defines a passageway and includes one or more apertures 132. Oral engagement assembly 110 further includes a diagnostic receptacle 140 insertable into the opening of handle 120 and the passageway of support 130.

Diagnostic receptacle 140 includes a gripping portion 144 attached to an elongated stick 142 including one or more diagnostic sensors 146. Diagnostic sensor 146 can be fixedly or removably inserted in (e.g., attached to) elongated stick 142 of diagnostic receptacle 140. Alternatively, diagnostic receptacle 140 can include one or more fluid capturing mechanisms in addition to or in place of diagnostic sensor 146.

As further shown in FIG. 6, support 130 does not include any bristles. However, support 130 can have any suitable shape for fitting into an animal's mouth. In addition, support 130 can have any suitable texture surface 134, for example, adapted to mechanically clean the surface of the teeth of the animal when rubbed against the teeth. In an embodiment, support 130 can be coated with a deodorant, teeth cleaning product or oral antiseptic.

Figure 7:
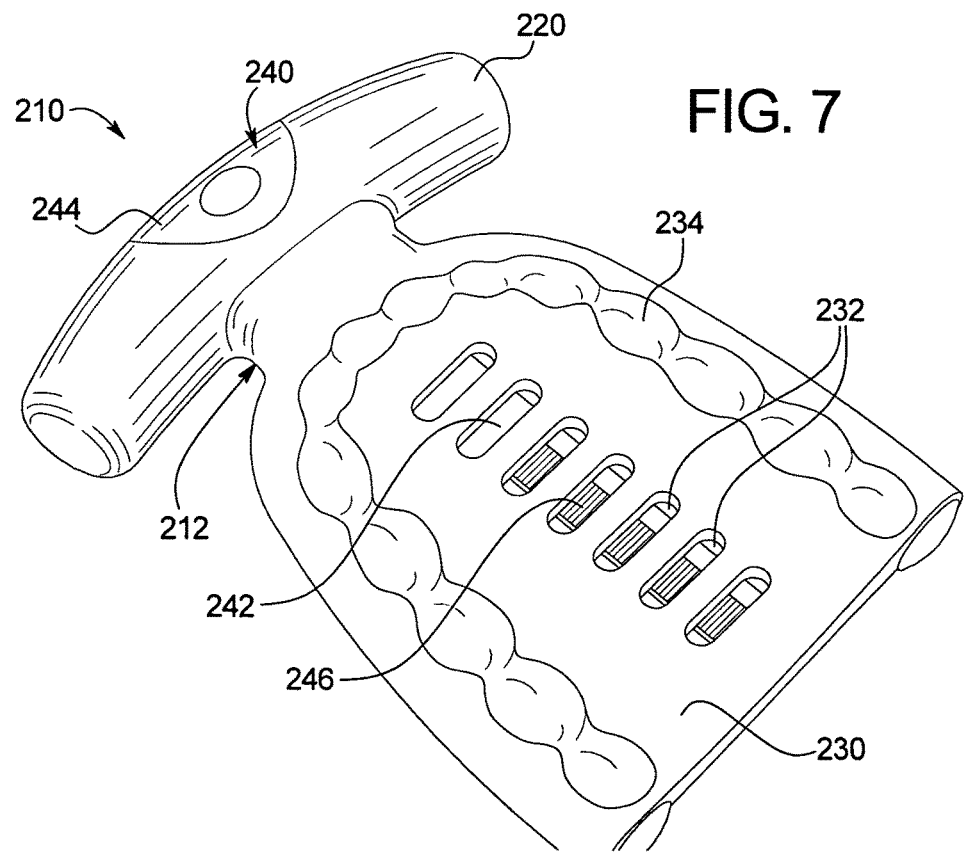
FIG. 7 shows a perspective view of an oral engagement assembly in a third embodiment of the invention.

In another aspect, as illustrated in FIG. 7, the invention provides an oral engagement assembly 210 including a mouth-piece 212 having a handle 220 defining an opening and a support 230 attached to handle 220. Support 230 defines a passageway and includes one or more apertures 232. Oral engagement assembly 210 further includes a diagnostic receptacle 240 insertable into the opening of handle 120 and the passageway of support 130.

Diagnostic receptacle 240 includes a gripping portion 244 attached to an elongated stick 242 including one or more diagnostic sensors 246. Diagnostic sensor 246 can be fixedly or removably inserted in (e.g., attached to) elongated stick 242 of diagnostic receptacle 240. Alternatively, diagnostic receptacle 240 can include one or more fluid capturing mechanisms in addition to or in place of diagnostic sensor 246.

As further shown in FIG. 7, support 230 is in the shape of a retainer constructed and arranged to fit an animal's teeth. For example, retainer-shaped support 230 can define a recessed surface 234 that is contoured to match the shape of an animal's upper and/or lower set of teeth. Retainer-shaped support 203 can have any suitable size and teeth design depending on the targeted animal (e.g., large dog, small dog, cat, puppy, etc.). In an embodiment, retainer-shaped support 230 can be coated with a deodorant, teeth cleaning product or oral antiseptic.

In a further aspect, the invention provides a method of collecting oral fluid from an animal. The method comprises providing an oral engagement assembly including 1) a mouth-piece including a handle defining an opening and a support attached to the handle, the support defining a passageway and including at least one aperture, and 2) a diagnostic receptacle insertable into the opening of the handle and the passageway of the support. The diagnostic receptacle includes a fluid capturing mechanism such as, for example, a tray, sponge, etc., to form an oral sample collector.

The method further provides inserting the oral engagement assembly into the mouth of an animal and removing the oral engagement assembly after a sufficient amount of oral fluid has been collected on the oral sample collector. In an embodiment, the method can further comprise testing the oral fluid collected on the oral sample collector using a fluid diagnostic tool. Alternatively, the oral sample collector can be sent for tests to a hospital or laboratory. In addition, the diagnostic receptacle in this method can include one or more diagnostic sensors.

In yet another aspect, the invention provides a method of diagnosing a condition or disease in an animal. For example, any condition or disease that can be diagnosed from oral fluid (e.g., ketosis) can be tested for with this method. The method comprises providing an oral engagement assembly including 1) a mouth-piece including a handle defining an opening and a support attached to the handle, the support defining a passageway and including at least one aperture, and 2) a diagnostic receptacle insertable into the opening of the handle and the passageway of the support. The diagnostic receptacle includes a diagnostic sensor fixedly or removably inserted in (e.g., attached to) the diagnostic receptacle.

The method further comprises inserting the oral engagement assembly into the mouth of an animal, removing the oral engagement assembly after a sufficient amount of time has passed for the diagnostic sensor to indicate a diagnosis or condition, and reading the diagnosis or condition from the diagnostic sensor. In some embodiments, the diagnostic sensor is read remotely, e.g., mailed or otherwise sent to a laboratory for analysis.

In an embodiment, the method can comprise comparing a color or pattern on the diagnostic sensor to a pattern on a diagnostic chart to determine the diagnosis or condition of the animal. The diagnostic sensor can include a test strip for a health condition related to, for example, dental, digestion, diabetes, halitosis, and combinations thereof or any other desired health condition. The diagnostic receptacle in this method can also include a fluid capturing mechanism.

In another aspect, the invention provides a method of improving the oral health of an animal. For example, the oral health can be related to cleaning teeth and/or massaging and strengthening the teeth and gums of the animal. The method comprises providing an oral engagement assembly including 1) a mouth-piece including a handle defining an opening and a support attached to the handle, the support defining a passageway and including at least one aperture, and 2) a diagnostic receptacle insertable into the opening of the handle and the passageway of the support.

The method further comprises inserting the oral engagement assembly into the mouth of the animal, causing the animal to grasp the oral engagement assembly with its teeth, and moving the oral engagement assembly in any suitable direction (e.g., tugging, pushing, lifting) so that the oral engagement assembly brushes against the teeth of the animal to mechanically clean the teeth. The support can include a plurality of bristles and/or a textured surface capable of sufficiently cleaning the teeth of the animal.

In a further aspect, the invention provides kits useful for producing and using the oral engagement assemblies of the invention. The kits comprise in separate containers in a single package or in separate containers in a virtual package, as appropriate for the kit component, either (A) a mouth-piece including a handle defining an opening and a support attached to the handle and comprising at least one aperture, a diagnostic receptacle insertable into the opening of the handle and the passageway of the support, and a diagnostic sensor insertable into the diagnostic receptacle; or (B) a mouth-piece including a handle defining an opening and a support attached to the handle and comprising at least one aperture, a diagnostic receptacle insertable into the opening of the handle, and at least one of (1) a diagnostic sensor configured to be insertable into the diagnostic receptacle for diagnosing the health of an animal; (2) a diagnostic chart to be used with the diagnostic sensor; (3) instructions on how to use the mouth-piece for strengthening teeth of an animal; (4) instructions on how to improve oral hygiene of an animal using the mouth-piece and the diagnostic receptacle; (5) instructions on how to use the diagnostic receptacle to screen an animal for a medical condition; (6) instructions on how to obtain technical assistance to use the mouth-piece and the diagnostic receptacle; (7) instructions on where to send the diagnostic receptacle for further testing of the oral fluid contained on the diagnostic receptacle; (8) an additional diagnostic receptacle for testing a specific medical condition of an animal; and (9) an oral fluid diagnostic tool to test oral fluid collected by the diagnostic receptacle.

When the kits comprise a virtual package, the kits are limited to instructions in a virtual environment in combination with one or more physical kit components. The kits may contain the kit components in any of various combinations. In one embodiment, the kit contains a mouth-piece and a diagnostic receptacle. In this embodiment, one or more diagnostic sensors associated with the diagnostic receptacle can be sold with this kit or sold separately from the kit, for example, as part of a virtual kit. Alternatively, the diagnostic sensor can be fixedly attached to the diagnostic receptacle in the kit to form an integrated diagnostic device.

In another, the kit contains a mouth-piece, a diagnostic receptacle and a diagnostic chart. In another, the kit contains a mouth-piece, a diagnostic receptacle, a diagnostic chart and an oral fluid diagnostic tool. In a further, the kit contains an oral engagement assembly and a package of diagnostic charts. Many other such combinations, including combinations including various instructions and diagnostic receptacles, are encompassed within the invention.

The kits can encompass one or more kit components that are ordered and shipped separately to a consumer, e.g., an order on the internet or by phone for a mouth-piece and a diagnostic receptacle, wherein the two articles are shipped from separate locations to the consumer's address. In all embodiments, the mouth-piece and the diagnostic receptacle may be attachable and detachable so that they can be used to produce an oral engagement assembly of the invention.

In a further aspect, the invention provides a means for communicating information about or instructions for one or more of (1) assembling a mouth-piece and a diagnostic receptacle to produce the oral engagement assembly; (2) using the oral engagement assembly to strengthen teeth of an animal; (3) using the oral engagement assembly to improve oral health of an animal; (4) using the oral engagement assembly to diagnose overall health of an animal; (5) using the oral engagement assembly to screen for a medical condition of an animal; (6) using the kits to produce an oral engagement assembly; and (7) obtaining technical assistance to produce or use the oral engagement assembly.

The communication means is a document, digital storage media, optical storage media, audio presentation, or visual display containing the information or instructions. In certain embodiments, the communication means can be a displayed website, a visual display kiosk, a brochure, a product label, a package insert, an advertisement, a handout, a public announcement, an audiotape, a videotape, digital streaming, a DVD, a CD-ROM, a computer readable chip, a computer readable card, a computer readable disk, a USB device, a FireWire device, a computer memory, and any combination thereof.

Useful information includes one or more of contact information for consumers to use if they have a question about the invention and its use. The communication means is useful for instructing on the benefits of using the present invention and communicating the approved methods for using the invention for the benefit of the animal using the oral engagement assembly.

In another aspect, the invention provides packages useful for containing an oral engagement assembly of the invention. The packages comprise at least one material suitable for containing the oral engagement assembly and a label affixed to the material containing a word or words, picture, design, acronym, slogan, phrase, or other device, or combination thereof, that indicates that the packages contain the oral engagement assembly. Typically, such device comprises the words "diagnostic device" or "oral diagnostic device" or "breath tester" or "saliva diagnostic" or an equivalent expression printed on the material. Any package configuration and packaging material suitable for containing the oral engagement assembly are useful in the invention, e.g., a bag, box, bottle, can, pouch, and the like manufactured from paper, plastic, foil, metal, and the like. In preferred embodiments, the packages further comprise an oral engagement assembly of the invention. In various embodiments, the packages further comprise at least one window that permit the package contents to be viewed without opening the package. In some embodiments, the window is a transparent portion of the packaging material. In others, the window is a missing portion of the packaging material.

In another aspect, the invention provides diagnostic sensors suitable for diagnosing a condition or disease in an animal. The diagnostic sensors comprise a diagnostic sensor configured to exactly match a sensor receiver in a diagnostic receptacle 40 of an oral engagement assembly of the invention, wherein the sensor receiver is configured to exactly match the configured sensor. The sensor receiver can have any suitable shape or configuration, e.g., square, oval, rectangular, circle, and the like. In some embodiments, the sensor and sensor receiver are configured to convey the image of an object that is indicative of a an animal being tested or a diagnostic test being performed, e.g., shaped like a canine paw to indicate the test is for a canine or like an animal muzzle to indicate that the test relates to breath testing. The diagnostic receptacle 40 can have two or more such configurations to permit it to be used for multiple tests, wherein the configurations assist the user in ensuring the desired test is being performed.

In another aspect, the invention provides oral sample collectors suitable for collecting oral fluids from an animal, e.g., saliva. The oral sample collectors comprise an oral sample collector configured to exactly match an oral sample collector receiver in a diagnostic receptacle 40 of an oral engagement assembly of the invention, wherein the sensor receiver is configured to exactly match the configured oral sample collector. The oral sample collector can have any suitable shape or configuration, e.g., square, oval, rectangular, circle, and the like. In some embodiments, the oral sample collector and oral sample collector receiver are configured to convey the image of an object that is indicative of a an animal being tested or a diagnostic test being performed, e.g., shaped like a canine paw to indicate the test is for a canine or like an animal muzzle to indicate that the test relates to breath testing. The diagnostic receptacle 40 can have two or more such configurations to permit it to be used for collecting multiple samples, wherein the configurations assist the user in ensuring the desired test is being performed. Such oral sample collectors are particularly useful for collecting one or more oral fluid samples that will be sent to remote locations such as analytical laboratories.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

What is claimed is:

1. An oral engagement assembly comprising:
a mouth-piece comprising a handle defining an opening, the mouth-piece further comprising a support comprising a first end attached to the handle on an opposite side of the handle from the opening, a length of the support is defined by a distance from the first end of the support attached to the handle to a second end of the support opposite from the first end, the oral engagement assembly terminates at the second end of the support, the support comprising a top surface and a bottom surface opposite to the top surface that extend from the handle and define a passageway in fluid communication with the opening, the support has a thickness defined by a distance from the top surface to the bottom surface and has a width defined by a distance from one side of the support to an opposite side of the support, the passageway extends in a first direction within the support, the top surface of the support comprises a planar surface that extends from the second end toward the first end of the support, the planar surface provided by the top surface of the support comprises at least one aperture that extends in a second direction different than the first direction and from the passageway to the top surface of the support, and the at least one aperture is configured to direct oral fluid into the passageway, wherein the handle comprises a shaft that comprises the opening, and the shaft extends perpendicular to the first direction and has a length perpendicular to the first direction that is greater than the width of the support; and
a diagnostic receptacle insertable through the opening of the handle into the passageway of the support, and the passageway positions at least a portion of the diagnostic receptacle underneath the at least one aperture and between the bottom surface of the support and the at least one aperture.

2. The oral engagement assembly of claim 1 wherein the support comprises a plurality of bristles, at least a portion of the plurality of bristles are positioned on the top surface of the support and circumscribe the at least one aperture.

3. The oral engagement assembly of claim 1 wherein the top surface of the support comprises a recessed surface contoured to receive upper teeth of a pet animal.

4. The oral engagement assembly of claim 1 wherein the diagnostic receptacle comprises at least one diagnostic sensor releasably inserted in the diagnostic receptacle.

5. The oral engagement assembly of claim 4 wherein the diagnostic sensor comprises a test strip for a health condition selected from the group consisting of dental, digestion, diabetes, halitosis, and combinations thereof.

6. The oral engagement assembly of claim 1 wherein the diagnostic receptacle comprises at least one diagnostic sensor fixedly attached to the diagnostic receptacle to form an integrated diagnostic device.

7. The oral engagement assembly of claim 6 wherein the diagnostic sensor comprises a test strip for a health condition selected from the group consisting of dental, digestion, diabetes, halitosis, and combinations thereof.

8. The oral engagement assembly of claim 1 wherein the diagnostic receptacle comprises a gripping portion attached to an elongated stick including at least one diagnostic sensor, and the gripping portion is flush with the shaft of the handle when the diagnostic receptacle is inserted through the opening of the handle into the passageway of the support.

9. The oral engagement assembly of claim 1 wherein the diagnostic receptacle comprises a fluid capturing mechanism to form an oral sample collector.

10. An oral engagement assembly comprising:
a mouth-piece comprising a handle defining an opening, the mouth-piece further comprising a support comprising a first end attached to the handle on an opposite side of the handle from the opening, a length of the support is defined by a distance from the first end of the support attached to the handle to a second end of the support opposite from the first end, the oral engagement assembly terminates at the second end of the support, and the support comprises a top surface and a bottom surface opposite to the top surface that extend from the handle and define a passageway in fluid communication with the opening, the support has a thickness defined by a distance from the top surface to the bottom surface and has a width defined by a distance from one side of the support to an opposite side of the support, the passageway extends from the opening in the handle into the support in a first direction, the top surface of the support comprises a planar surface that extends from the second end toward the first end of the support, the planar surface provided by the top surface of the support comprises an aperture that extends from the passageway to the top surface of the support in a second direction different than the first direction and configured to direct oral fluid into the passageway, wherein the handle comprises a shaft that comprises the opening, and the shaft extends perpendicular to the first direction and has a length perpendicular to the first direction that is greater than the width of the support; and a diagnostic receptacle configured to be insertable into the mouth-piece, the diagnostic receptacle comprising a diagnostic sensor releasably inserted in the diagnostic receptacle, and the passageway positions at least a portion of the diagnostic receptacle underneath the at least one aperture and between the bottom surface of the support and the at least one aperture.

11. An oral engagement assembly comprising:

a mouth-piece comprising a handle defining an opening, the mouth-piece further comprising a support comprising a first end attached to the handle on an opposite side of the handle from the opening, a length of the support is defined by a distance from the first end of the support attached to the handle to a second end of the support opposite from the first end, the oral engagement assembly terminates at the second end of the support, and the support comprises a top surface and a bottom surface opposite to the top surface that extend from the handle and define a passageway in fluid communication with the opening in the handle, the support has a thickness defined by a distance from the top surface to the bottom surface and has a width defined by a distance from one side of the support to an opposite side of the support, the passageway extending from the opening in the handle into the support in a first direction, the top surface of the support comprises a planar surface that extends from the second end toward the first end of the support, the planar surface provided by the top surface of the support comprises an aperture that extends from the passageway to the top surface of the support in a second direction different than the first direction, the aperture configured to direct oral fluid into the passageway, the opening and the aperture arranged at different positions relative to each other, wherein the handle comprises a shaft that comprises the opening, and the shaft extends perpendicular to the first direction and has a length perpendicular to the first direction that is greater than the width of the support; and an integrated diagnostic device configured to be inserted through the opening into the mouth-piece such that the aperture is above the integrated diagnostic device, the integrated diagnostic device comprising a diagnostic receptacle comprising at least one diagnostic sensor fixedly attached to the diagnostic receptacle, and the passageway positions at least a portion of the diagnostic receptacle underneath the at least one aperture and between the bottom surface of the support and the at least one aperture.

12. An oral engagement assembly comprising:

a mouth-piece comprising a handle defining an opening, the mouth-piece further comprising a support comprising a first end attached to the handle on an opposite side of the handle from the opening, a length of the support is defined by a distance from the first end of the support attached to the handle to a second end of the support opposite from the first end, the oral engagement assembly terminates at the second end of the support, the support comprises a top surface and a bottom surface opposite to the top surface that extend from the handle and define a passageway that emerges from the mouth-piece at an opening in the handle and at an aperture in the top surface of the support, the support has a thickness defined by a distance from the top surface to the bottom surface and has a width defined by a distance from one side of the support to an opposite side of the support, the top surface of the support comprises a planar surface that extends from the second end toward the first end of the support, the opening and the aperture are arranged at different positions relative to each other, the opening of the handle is in fluid communication with the passageway, the aperture configured to direct oral fluid into the passageway, wherein the handle comprises a shaft that comprises the opening, and the shaft extends perpendicular to the first direction and has a length perpendicular to the first direction that is greater than the width of the support; and a diagnostic sensor configured to be insertable into a diagnostic receptacle that is configured to be insertable through the opening into the mouth-piece such that the aperture is between the integrated diagnostic receptacle and the exterior of the mouth-piece, and the passageway positions at least a portion of the diagnostic receptacle underneath the at least one aperture and between the bottom surface of the support and the at least one aperture.

13. The diagnostic sensor of claim 12 wherein the diagnostic sensor comprises a test strip for a health condition selected from the group consisting of dental, digestion, diabetes, halitosis, and combinations thereof.

14. A method of collecting oral fluid from a pet animal, the method comprising:

providing an oral engagement assembly comprising 1) a mouth-piece comprising a handle defining an opening, the mouth-piece further comprising a support attached to the handle on an opposite side of the handle from the opening, the support defines a passageway in fluid communication with the opening of the handle, a top surface of the support comprising at least one aperture configured to direct oral fluid into the passageway, and 2) a diagnostic receptacle insertable through the opening of the handle into the passageway of the support, the diagnostic receptacle comprising a fluid capturing mechanism that forms an oral sample collector;

collecting oral fluid from the pet animal through the at least one aperture onto the fluid capturing mechanism by inserting the support into the mouth of the pet animal and holding the handle of the oral engagement assembly while the pet animal bites into and tugs on the support; and removing the oral engagement assembly from the mouth of the pet animal after a sufficient amount of the oral fluid has been collected on the oral sample collector.

15. The method of claim 14 comprising testing the oral fluid collected on the oral sample collector using a fluid diagnostic tool.

16. The method of claim 14 wherein the diagnostic receptacle comprises at least one diagnostic sensor releasably inserted in the diagnostic receptacle.

17. The method of claim 14 wherein the diagnostic receptacle comprises at least one diagnostic sensor fixedly attached to the diagnostic receptacle to form an integrated diagnostic device.

18. A method of diagnosing a condition or disease in a pet animal, the method comprising:

providing an oral engagement assembly comprising 1) a mouth-piece comprising a handle defining an opening, the mouth-piece further comprising a support attached to the handle on an opposite side of the handle from the opening, the support defining a passageway in fluid communication with the opening, the passageway extending from the opening into the support, a top surface of the support comprising at least one aperture configured to direct oral fluid into the passageway, and 2) a diagnostic receptacle insertable through the opening of the handle into the passageway of the support, the diagnostic receptacle comprising at least one diagnostic sensor;

directing oral fluid of the pet animal through the at least one aperture to the diagnostic receptacle by inserting the support into the mouth of the pet animal and holding the handle of the oral engagement assembly while the pet animal bites into and tugs on the support;

removing the oral engagement assembly from the mouth of the pet animal after a sufficient amount of time has passed for the diagnostic sensor to indicate a diagnosis or condition; and reading the diagnosis or condition from the diagnostic sensor.

19. The method of claim 18 comprising comparing a color or pattern on the diagnostic sensor to a pattern on a diagnostic chart to determine the diagnosis or condition of the animal.

20. The method of claim 18 wherein the diagnostic sensor comprises a test strip for a health condition selected from the group consisting of dental, digestion, diabetes, halitosis, and combinations thereof.

21. The method of claim 18 wherein the diagnostic receptacle comprises a fluid capturing mechanism to form an oral sample collector.

22. A method of improving the oral health of a pet animal, the method comprising:

providing an oral engagement assembly comprising 1) a mouth-piece comprising a handle defining an opening, the mouth-piece further comprising a support attached to the handle on an opposite side of the handle from the opening, the support defining a passageway in fluid communication with the opening, the passageway extending from the opening into the support, a top surface of the support comprising at least one aperture configured to direct oral fluid into the passageway, and 2) a diagnostic receptacle insertable through the opening of the handle into the passageway of the support;

inserting the support into a mouth of the pet animal;

causing the pet animal to grasp the support with teeth of the pet animal; and moving the oral engagement assembly by moving the handle relative to the mouth of the pet animal while the mouth of the pet animal bites into and tugs on the support so that the oral engagement assembly brushes against the teeth of the pet animal and oral fluid passes through the at least one aperture to the diagnostic receptacle.

23. The method of claim 22 wherein the support comprises a bottom surface opposite to the top surface and further comprises a plurality of bristles, at least a portion of the plurality of bristles circumscribe the at least one aperture, and the oral engagement assembly is inserted into the mouth of the pet animal such that the top surface of the support faces an upper portion of the mouth and the bottom surface of the support faces a lower portion of the mouth.

* * * * *